United States Patent
Edwards et al.

(10) Patent No.: US 9,655,702 B2
(45) Date of Patent: May 23, 2017

(54) NON-PRESSURIZED SYSTEM FOR CREATING LIQUID DROPLETS IN A DENTAL CLEANING APPLIANCE

(71) Applicant: KONINKLIJKE PHILIPS N.V., Eindhoven (NL)

(72) Inventors: Dainia Edwards, Issaquah, WA (US); Tyler G. Kloster, Snoqualmie, WA (US); Wolter F. Benning, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 412 days.

(21) Appl. No.: 14/277,866

(22) Filed: May 15, 2014

(65) Prior Publication Data
US 2014/0248579 A1    Sep. 4, 2014

Related U.S. Application Data

(63) Continuation of application No. 13/139,625, filed as application No. PCT/IB2009/055518 on Dec. 4, 2009, now Pat. No. 8,753,117.

(51) Int. Cl.
| | | |
|---|---|---|
| *A61C 17/02* | (2006.01) | |
| *A61C 1/00* | (2006.01) | |
| *A61C 15/00* | (2006.01) | |
| *A61C 17/028* | (2006.01) | |

(52) U.S. Cl.
CPC ........ *A61C 17/0202* (2013.01); *A61C 1/0084* (2013.01); *A61C 1/0092* (2013.01); *A61C 15/00* (2013.01); *A61C 17/028* (2013.01)

(58) Field of Classification Search
CPC ... A61C 1/0084; A61C 1/0092; A61C 17/028; A61C 17/0202; A61C 15/00
See application file for complete search history.

(56) References Cited

U.S. PATENT DOCUMENTS

| 601,616 A | 3/1898 | Gurnee |
|---|---|---|
| 1,838,873 A | 12/1931 | Lewis |
| 3,703,170 A | 11/1972 | Ryckman, Jr. |

(Continued)

FOREIGN PATENT DOCUMENTS

| CN | 201082201 Y | 7/2008 |
|---|---|---|
| DE | 19645643 A1 | 5/1998 |

(Continued)

*Primary Examiner* — Ralph Lewis

(57) ABSTRACT

The appliance (10, FIG. 1) includes a body portion (27) and a nozzle portion (30) through which a spray of liquid droplets exits from a distal end thereof for cleaning of dental regions. The nozzle includes an orifice (36) at a proximal end thereof adjacent the body portion, as well as a pump (38) for moving liquid into an area of the nozzle just forward of the orifice. A mechanical system (12, 13, 14) is provided for moving a plunger or piston element (16) first away from the orifice under tension, such as a compression spring (24), and then controllably releasing the plunger or piston toward the orifice, the plunger/piston moving with sufficient force that atmospheric air which has been drawn into the appliance between the plunger or piston is forced through the orifice at a sufficiently high rate of speed to produce a spray of fluid droplets for dental cleaning when the moving air comes into contact with the liquid in the nozzle.

3 Claims, 3 Drawing Sheets

(56) References Cited

U.S. PATENT DOCUMENTS

| | | | |
|---|---|---|---|
| 3,870,039 A | 3/1975 | Moret et al. | |
| 5,014,884 A | 5/1991 | Wunsch | |
| 5,997,518 A | 12/1999 | Laibovitz et al. | |
| 6,139,319 A | 10/2000 | Sauer et al. | |
| 6,591,832 B1 | 7/2003 | DeJonge | |
| 7,025,056 B2 | 4/2006 | Eason et al. | |
| 8,753,117 B2 * | 6/2014 | Edwards | A61C 1/0084 239/359 |
| 2004/0106083 A1 | 6/2004 | Pond | |
| 2006/0078844 A1 | 4/2006 | Goldman et al. | |
| 2007/0095942 A1 | 5/2007 | Ray et al. | |
| 2008/0014548 A1 | 1/2008 | Paxton | |
| 2009/0017423 A1 | 1/2009 | Gottenbos et al. | |
| 2010/0273126 A1 | 10/2010 | Janssen et al. | |
| 2011/0207078 A1 | 8/2011 | Johnson et al. | |

FOREIGN PATENT DOCUMENTS

| | | | |
|---|---|---|---|
| GB | 1487639 A | 10/1977 | |
| JP | H0636614 A | 2/1994 | |
| JP | 2000157562 A | 6/2000 | |
| SU | 1752436 A1 | 8/1992 | |
| WO | 2005016550 A1 | 2/2005 | |
| WO | 2006067760 A1 | 6/2006 | |
| WO | 2006090229 A1 | 8/2006 | |
| WO | 2008001301 A2 | 1/2008 | |

* cited by examiner

NON-PRESSURIZED SYSTEM FOR CREATING LIQUID DROPLETS IN A DENTAL CLEANING APPLIANCE

CROSS-REFERENCE TO PRIOR APPLICATIONS

This application is a Continuation of prior U.S. patent application Ser. No. 13/139,625, filed Jun. 14, 2011, which is a National Stage Application of PCT/IB2009/055518, filed on Dec. 4, 2009, which claims the benefit of U.S. Provisional Application Ser. No. 12/344,852, filed on Dec. 29, 2008. These applications are hereby incorporated by reference herein.

This invention relates generally to liquid droplet dental cleaners, and more specifically concerns a non-pressurized system for creating a droplet spray for dental cleaning.

Dental cleaners using a spray of liquid droplets to clean dental regions of the teeth, including interproximal areas, are known. In many such appliances, a stream of high velocity gas is used to create the liquid droplets when liquid is brought into contact with the gas stream, such as by a pump or other arrangement.

Typically, the high velocity gas stream uses compressed gas, such as from a cartridge source, to provide the energy necessary for the gas stream. A compressed gas appliance is generally effective to produce liquid droplets for cleaning. However, compressed gas does have known limitations, including safety limitations and objections by some users to the taste of the resulting liquid droplets. The depleted gas cartridges must also be disposed of safely and in an environmentally appropriate manner, which can be inconvenient.

Hence, it would be desirable to have a liquid droplet dental appliance which is capable of producing liquid droplets for cleaning with a non-pressurized source of gas, in particular without the need for a compressed gas consumable cartridge.

Accordingly, the invention is a fluid droplet appliance for dental cleaning, comprising: a dental cleaning appliance having a body portion and a nozzle portion for exit of a spray of liquid droplets from a distal end thereof; a liquid reservoir wherein in operation liquid is moved from the reservoir into an area of the nozzle near an open proximal end thereof; and a system for driving a plunger or piston element toward the proximal end of the nozzle with sufficient force that air acted on by the plunger or piston element is forced or released into the nozzle at a high rate of speed, sufficient to create a spray of liquid droplets when the moving air comes into contact with the liquid.

Figure 1:
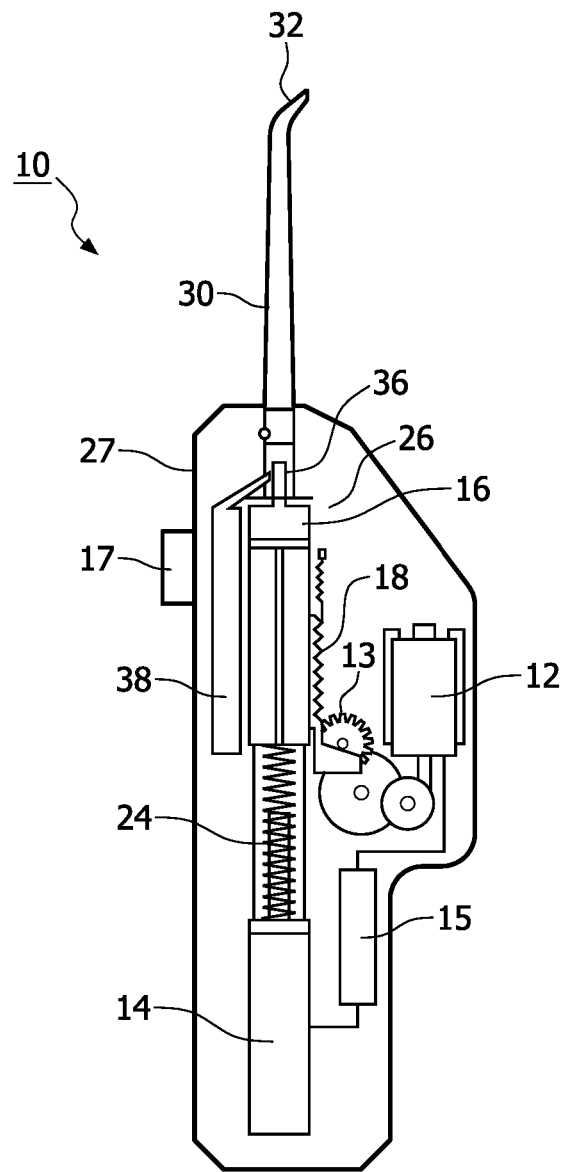
FIG. 1 is a schematic view of a first embodiment of a non-pressurized liquid droplet appliance.

FIG. 1 shows an appliance 10 which uses a mechanical spring-drive system to create a liquid droplet spray for dental cleaning. The appliance includes a motor and gear train arrangement 12, with a drive gear 13, the motor being powered by a battery 14. A control unit 15 is included between the battery and the motor for control of the operation of the appliance. A button or similar element 17 is used to actuate the appliance. The gear train drives a plunger/piston member 16 with drive gear 13 engaging a gear rack 18 on plunger/piston 16. As the drive gear 12 rotates, plunger/piston 16 is moved to the rear of the appliance 10 against the action of a compression spring 24. At the same time, air is drawn into a chamber 26 in the appliance, which could be the interior of the appliance, or a separate volume within the interior of the appliance.

The appliance includes an elongated nozzle 30 which extends outwardly from the appliance and typically has a curved portion 32 at the distal end thereof, through which a spray of liquid droplets is directed for cleaning action against dental regions of the teeth. The curved portion 32 assists in convenient positioning of the nozzle 30 in the mouth by the user. At a proximal end of the nozzle adjacent body 27 of the appliance is an orifice 36. Orifice 36 can vary in size, typically between 0.5 mm and 10 mm. As indicated above, when the plunger/piston 16 is moved to the rear by the action of the motor and gear train 12, air is drawn into chamber 26, either through orifice 36 or alternatively, through a one-way check valve in the body 27 of the appliance, which communicates with chamber 26.

A reservoir 38 for water or other liquid is also present in the appliance. Liquid in reservoir 38 is moved to the vicinity of the orifice 36 within the nozzle, typically by a pump or by passive aspiration or other means.

Drive gear 13 in the embodiment shown has an open space (teeth missing) at a selected position on its periphery, such that when the open space comes adjacent the gear rack 18 on the plunger/piston, the plunger releases, since there are no meshed gears to hold it back, at high speed toward orifice 36 by the action of compression spring 24 moving toward its rest (non-compressed) position. This action is sufficient to drive the air in chamber 26 at high speed through orifice 36. When the fast-moving air comes into contact with the liquid which is adjacent orifice 36, a spray of liquid droplets is produced.

The liquid droplets can be of various sizes, and the speed of the droplets can vary from relatively low speed, e.g. 10 meters per second, to a high speed of 200 meters per second or even greater. Typically, however, a 50 m/sec droplet velocity with droplets in a size range of 5 microns-0.5 mm will provide effective dental cleaning.

Figure 2:
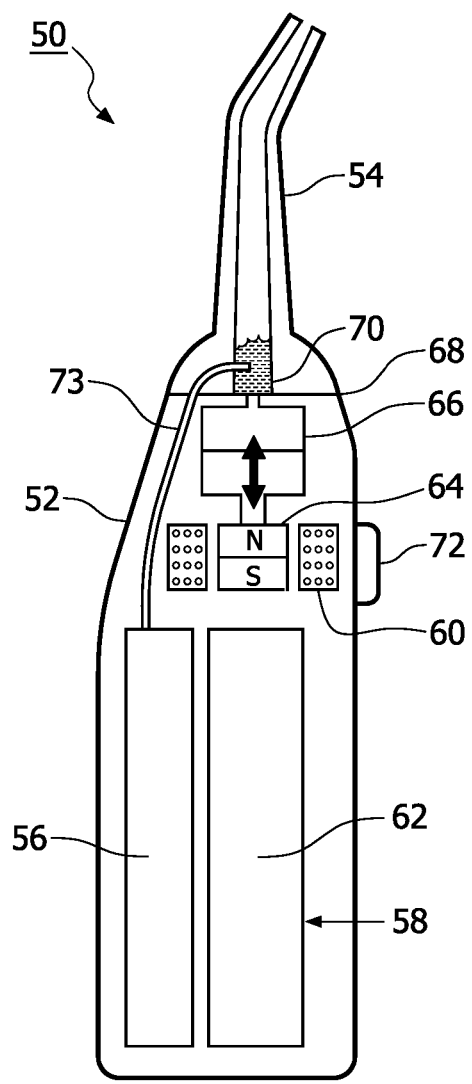
FIG. 2 is a schematic view of another embodiment.

FIG. 2 shows another non-pressurized gas drive embodiment, generally referred to as a voice coil drive. The appliance is shown generally at 50. It includes a body portion 52 and a nozzle portion 54 which extends forwardly from the body portion. Body portion 52 includes an actuating element 72. Positioned within body portion 52 are a water reservoir 56 and a battery and circuit (electronics) portion 58. The battery and circuit portion 58 connects to a voice coil assembly 60, providing an energizing signal thereto. The battery and circuit portion 58 includes a capacitor 62. Voice coil 60 encircles a magnet 64. Connected to magnet 64 and positioned between magnet 64 and the proximal end of nozzle portion 54 is a piston 66. At the proximal end 68 of nozzle portion 54, adjacent body portion 52, is a nozzle orifice 70. Orifice 70 is typically 0.5-10 mm in diameter.

In operation in one arrangement, the user operates button 72. This energizes the voice coil 60, which pulls magnet 64 rearwardly, which in turn pulls piston 66 toward the rear of the appliance. When the piston is moved rearwardly, air moves into the interior of the body portion 52, either through orifice 70 or through a one-way valve in the body portion. The air could move into the interior of the appliance, or into a chamber within the appliance. The capacitor 62 also begins to charge. When the charge reaches a certain preselected level, the capacitor discharges into the voice coil which drives the magnet forward, pushing the piston toward the orifice.

In another arrangement, the voice coil maintains the magnet and the piston in a rear position prior to operation of button 72. When button 72 is operated, the capacitor begins to charge, until it reaches a selected charge level, at which point the capacitor discharges into the voice coil, which drives the magnet and the piston forwardly.

Sufficient force is produced by the piston in each arrangement to force air at high speed through orifice 70. The air forced through the orifice contacts liquid which is directed into the lower end of the nozzle through line 73 by means of a pump or the like. Droplets are created by the interaction of the fast-moving air and the liquid. The droplets created will vary in size. In this arrangement, the droplets will be, for instance, between 5 microns –0.5 mm. The gas stream will further help to move the droplets through the nozzle and out toward the teeth for cleaning.

Figure 3:
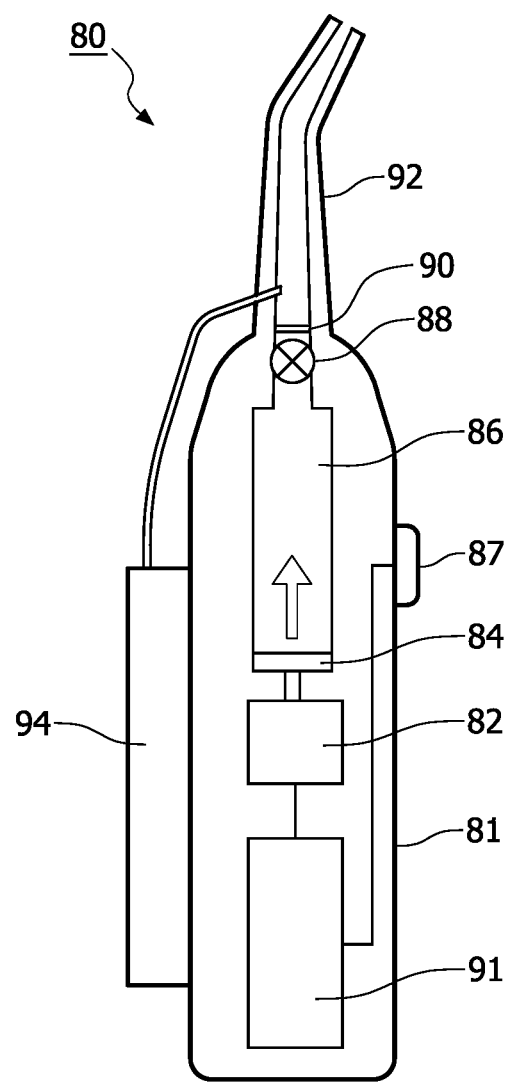
FIG. 3 is a schematic view of another embodiment.

In still another arrangement, referring to FIG. 3, an appliance 80 includes in a body portion 81 a pump 82 which acts on a piston 84 in a cylinder 86, to compress air to a specified pressure in a volumetric valve 88. Operation is initiated by a button 87; power is provided by a battery 91. When a specified pressure is reached, the valve is released, with the compressed air being forced through an orifice 90 to contact liquid in a lower portion of a nozzle portion 92. Droplets are created by the interaction of the fast-moving gas and the liquid and move through the exit 94 of nozzle 92.

Accordingly, several embodiments have been described which produce a spray of liquid droplets through a nozzle for dental cleaning without the use of a pressurized gas system and with the use of atmospheric air.

Although a preferred embodiment of the invention has been disclosed for purposes of illustration, it should be understood that various changes, modifications and substitutions can be incorporated in the embodiment without departing from the spirit of the invention, which is defined by the claims which follow.

The invention claimed is:

1. A fluid droplet appliance for dental cleaning, comprising:
   a dental cleaning appliance having a body portion and a nozzle portion for exit of a spray of liquid droplets from a distal end thereof;
   a liquid reservoir wherein in operation liquid is moved from the reservoir into an area of the nozzle near an open proximal end thereof;
   a system for driving a plunger or piston element toward the proximal end of the nozzle with sufficient force that air acted on by the plunger or piston element is forced or released into the nozzle at a high rate of speed, sufficient to create a spray of liquid droplets when the moving air comes into contact with the liquid; and
   an orifice at a proximal end of the nozzle portion, through which air is forced by action of the plunger or piston element,
   wherein the system for moving a plunger or piston element includes a voice coil surrounding a magnet and a capacitor, wherein the magnet is connected to a piston member, and further including a source of power which charges the capacitor, wherein in operation the voice coil pulls the magnet to the rear of the appliance, away from the orifice, wherein discharge of the capacitor results in the magnet moving the plunger or piston member forwardly, forcing air through the orifice.

2. The fluid droplet appliance of claim 1, wherein the appliance includes a user-operated element to actuate the appliance.

3. The fluid droplet appliance of claim 1, wherein atmospheric air moves into the appliance by action of the piston being moved away from the orifice.

* * * * *